(12) United States Patent
Suh et al.

(10) Patent No.: US 7,436,992 B2
(45) Date of Patent: Oct. 14, 2008

(54) METHODS AND APPARATUS FOR TESTING A COMPONENT

(75) Inventors: Ui Won Suh, Cincinnati, OH (US); Gigi Olive Gambrell, West Chester, OH (US); John William Ertel, New Vienna, OH (US); William Stewart McKnight, Hamilton, OH (US)

(73) Assignee: General Electric Company, Schenectady, NY (US)

( * ) Notice: Subject to any disclaimer, the term of this patent is extended or adjusted under 35 U.S.C. 154(b) by 802 days.

(21) Appl. No.: 10/909,198

(22) Filed: Jul. 30, 2004

(65) Prior Publication Data

US 2006/0023961 A1  Feb. 2, 2006

(51) Int. Cl.
*G06K 9/00* (2006.01)
*G01N 27/82* (2006.01)
*H04N 7/18* (2006.01)

(52) U.S. Cl. ............... 382/141; 382/149; 324/238; 348/125

(58) Field of Classification Search ......... 382/141–152; 348/92, 125; 324/238
See application file for complete search history.

(56) References Cited

U.S. PATENT DOCUMENTS

| | | | |
|---|---|---|---|
| 4,591,784 A | 5/1986 | Kolitsch et al. | |
| 4,628,261 A | 12/1986 | Hüschelrath et al. | |
| 4,821,204 A | 4/1989 | Hüschelrath | |
| 4,995,958 A * | 2/1991 | Anderson et al. | 204/298.2 |
| 5,028,100 A | 7/1991 | Valleau et al. | |
| 5,059,904 A * | 10/1991 | Mazzone et al. | 324/226 |
| 5,161,413 A * | 11/1992 | Junker et al. | 73/634 |
| 5,182,775 A | 1/1993 | Matsui et al. | |
| 5,207,005 A * | 5/1993 | Amos et al. | 33/501.04 |
| 5,345,514 A | 9/1994 | Mahdavieh et al. | |
| 5,623,204 A * | 4/1997 | Wilkerson | 324/228 |
| 5,781,007 A * | 7/1998 | Partika et al. | 324/220 |
| 6,339,331 B1 * | 1/2002 | Ruzzo | 324/261 |
| 2004/0075429 A1 * | 4/2004 | Hiroshima | 324/242 |
| 2004/0153260 A1 * | 8/2004 | Suh et al. | 702/38 |

* cited by examiner

*Primary Examiner*—Daniel G Mariam
(74) *Attorney, Agent, or Firm*—William Scott Andes, Esq.; Armstrong Teasdale LLP

(57) ABSTRACT

A method for inspecting a component. The method includes generating a scan plan of a component to be inspected, coupling a side-mount probe to an eddy current inspection system, inducing an eddy current into the component, measuring the eddy current in the component to generate a plurality of scan data, and analyzing the scan data to generate at least one image of the component being inspected.

20 Claims, 10 Drawing Sheets

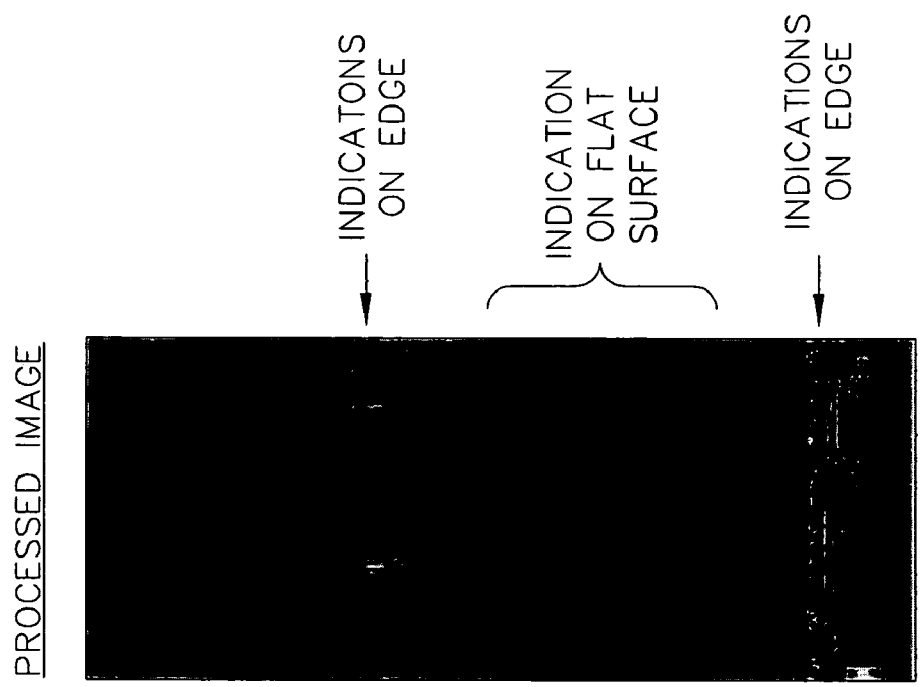
FIG. 16b
FIG. 16a
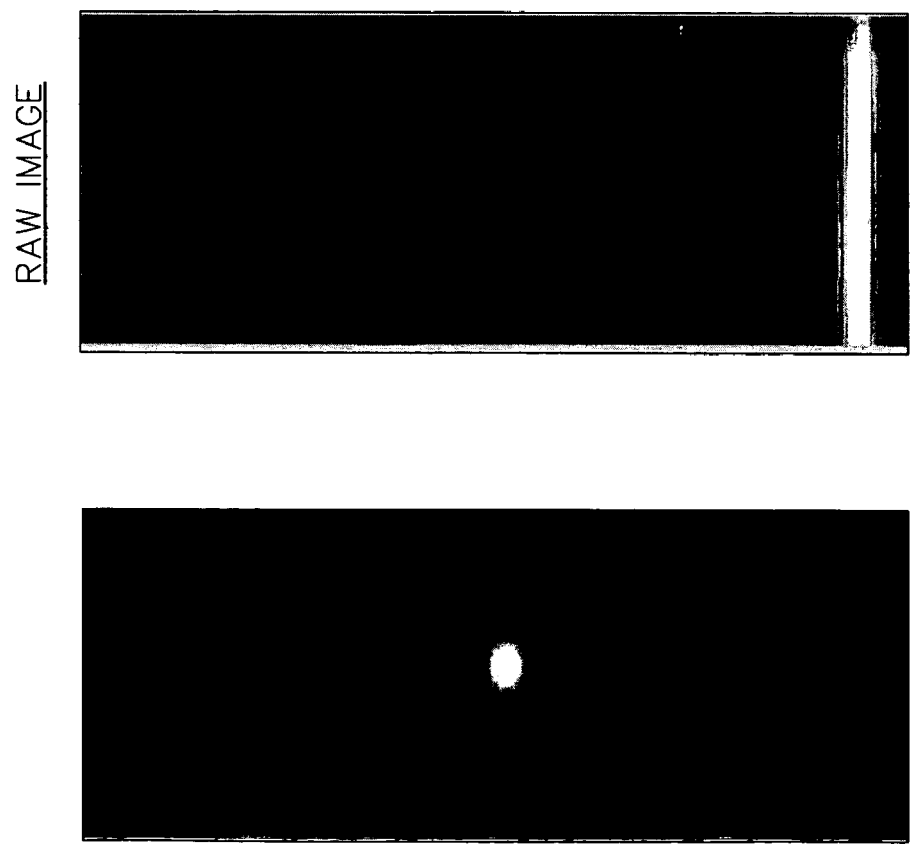
FIG. 15

METHODS AND APPARATUS FOR TESTING A COMPONENT

BACKGROUND OF THE INVENTION

This invention relates generally to the testing of components, and more particularly to methods and apparatus and for testing components having non-uniform surfaces.

Eddy current (EC) inspection devices are used to detect abnormal indications in a component under test such as, but not limited to, a gas turbine engine component. At least one known EC inspection device is used to detect cracks, pings, dings, raised material, and/or other surface imperfections on a surface of the component, and/or to evaluate material properties of the component including the conductivity, density, and/or degrees of heat treatment of the component.

During operation, known EC devices measure the interaction between an electromagnetic field generated by the EC device and the component being tested. For example, known EC devices include a probe coil that generates a magnetic field. When the coil is positioned adjacent to a conductive component, an eddy current is generated on the surface of the component. A flaw on and/or near the surface of the component generates a disruption in the eddy current field which produces a secondary field that is received by the eddy current probe coil or by a sensor coil in the eddy current probe which converts the altered secondary magnetic field to an electrical signal that may be recorded on a strip chart recorder for example.

At least one known EC device includes a relatively small coil that is typically 0.020 inches in diameter, that is used to detect surface flaws, surface contamination, material properties, and/or a surface roughness of the component being tested. In use, the coil is positioned normal to the surface of the component under test. A substantially constant pressure is applied to the probe as the coil moves along the surface of the component under test to facilitate maintaining an integrity of the signal generated by the EC device. However, when the EC device is not oriented normal to the surface of the component being tested, a "lift-off effect" may be created To facilitate reducing the lift-off-effect, at least one known EC device includes a dual-coil probe, e.g. a differential probe, having a pair of coils with an opposite polarity. Each coil in the dual-coil probe generates an electrical signal when the probe contacts a surface of the component being tested. When the dual coil probe passes over a smooth surface of the component being tested, the signals cancel each other. However, when the dual coil probe passes over a local physical abnormality on the surface, the probe generates a signal that is proportional to the size, depth, etc., of the physical abnormality.

When a non-continuous component surface feature is inspected, such as a feature on a rotating part, known differential probes may have difficulty resolving sharp curvatures, in such areas as corners and cusps. During operation, when such probes encounter a corner or cusp, the differential probe device may become skewed to the surface of the component, such that a resulting lift-off effect may cause a loss of usable data. Accordingly, known EC devices may be less effective in generating an accurate response when the EC device is used to detect an abnormal condition on a component having complex geometries, and/or a component having irregular conditions, especially in components including sharp indexing or objects that extend into the path of the probe such that the probe cannot consistently be placed normal to scan surface.

BRIEF DESCRIPTION OF THE INVENTION

In one aspect, a method for inspecting a component is provided. The method includes generating a scan plan of a component to be inspected, coupling a side-mount probe to an eddy current inspection system, inducing an eddy current into the component, measuring the eddy current in the component to generate a plurality of scan data, and analyzing the scan data to generate at least one image of the component being inspected.

In another aspect, a side-mount eddy current probe for inspecting a component is provided. The eddy current probe includes a body portion including an outer surface and having a width, and a length that is longer than the width, and a tip portion extending from the body portion, the tip portion including an end and an outer tip, the end extending between the body portion and the outer tip, the tip portion having a width and a length, the tip portion width gradually decreases from the tip portion end to the outer tip, the tip portion length gradually decreases from the tip portion end to the outer tip.

In a further aspect, an eddy current inspection system is provided. The inspection system includes an eddy current probe including a body portion including an outer surface and having a width, and a length that is longer than the width, and a tip portion extending from the body portion, the tip portion includes an end and an outer tip, the end extends between the body portion and the outer tip, the tip portion has a width and a length, the tip portion width gradually decreases from the end to the outer tip, the tip portion length gradually decreases from the end to the outer tip, and a data acquisition/control system coupled to the eddy current probe and configured to record an output received from the eddy current probe.

BRIEF DESCRIPTION OF THE DRAWINGS

FIG. 15 illustrates a component image generated using an eddy current probe;

FIGS. 16 and 16b illustrate exemplary images generated of a component that includes simulated indications.

DETAILED DESCRIPTION OF THE INVENTION

Figure 1:
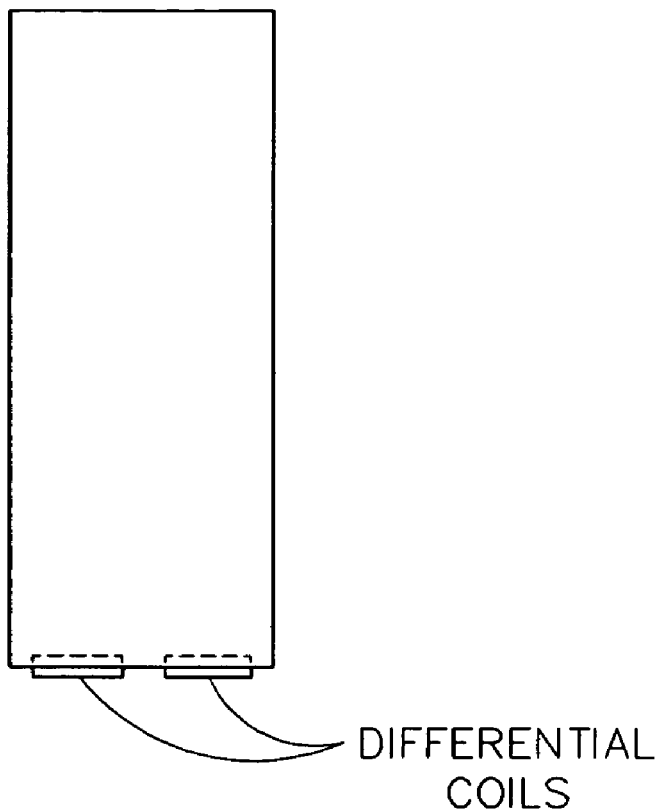
FIG. 1 is a front view of a known eddy current probe.
Figure 2:
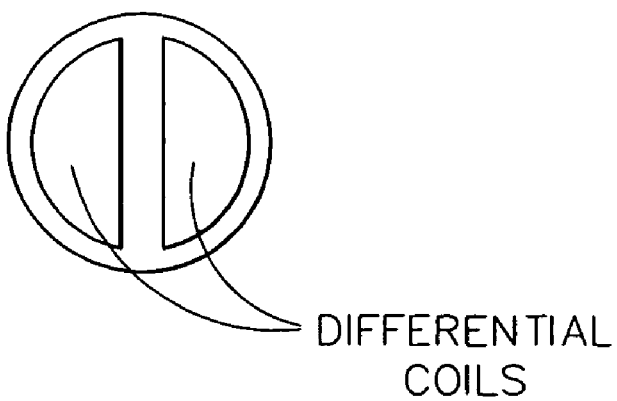
FIG. 2 is a top view of the known eddy current probe shown in FIG. 1.
Figure 3:
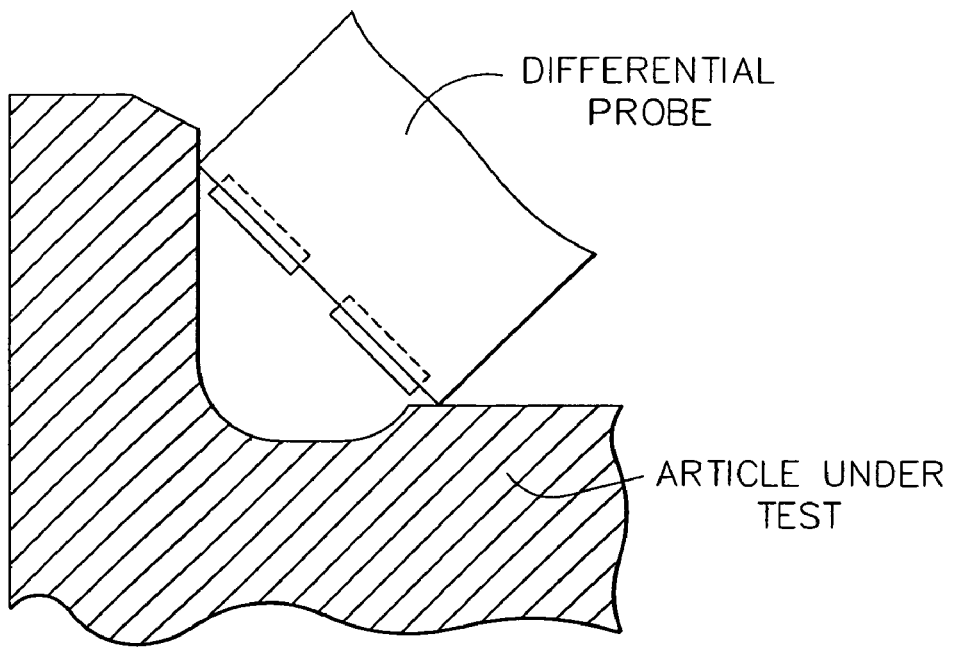
FIG. 3 is a front view of the known eddy current probe shown in FIG. 1 illustrating a lift-off effect in an indexing direction.
Figure 4:
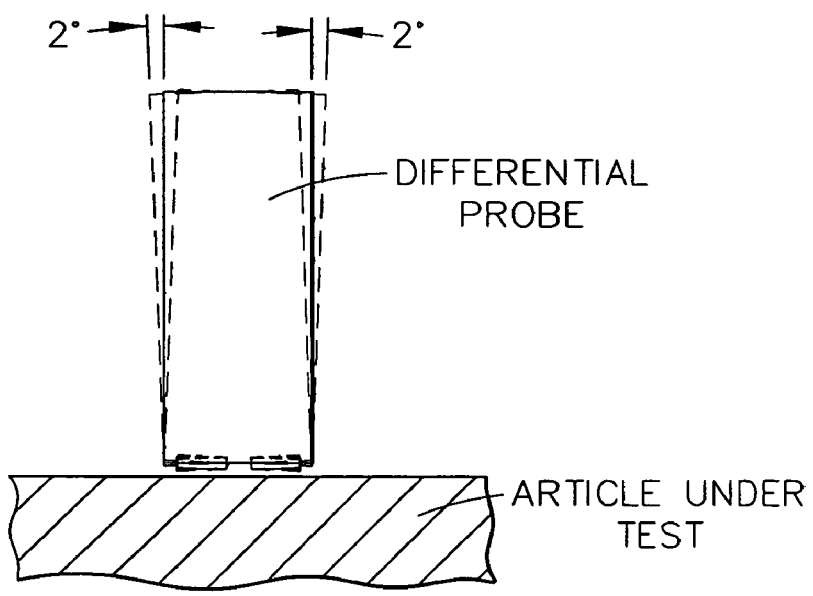
FIG. 4 is a front view of the known eddy current probe shown in FIG. 1 and illustrating a lift-off effect in a scan direction.

FIG. 1 is a front view of a known eddy current probe 500. FIG. 2 is a top view of eddy current probe 500 shown in FIG. 1. FIG. 3 is a front view of eddy current probe 500 shown in FIG. 1 illustrating a lift-off effect in an indexing direction. FIG. 4 is a front view of eddy current probe 500 shown in FIG. 1 and illustrating a lift-off effect in a scan direction.

Figure 5:
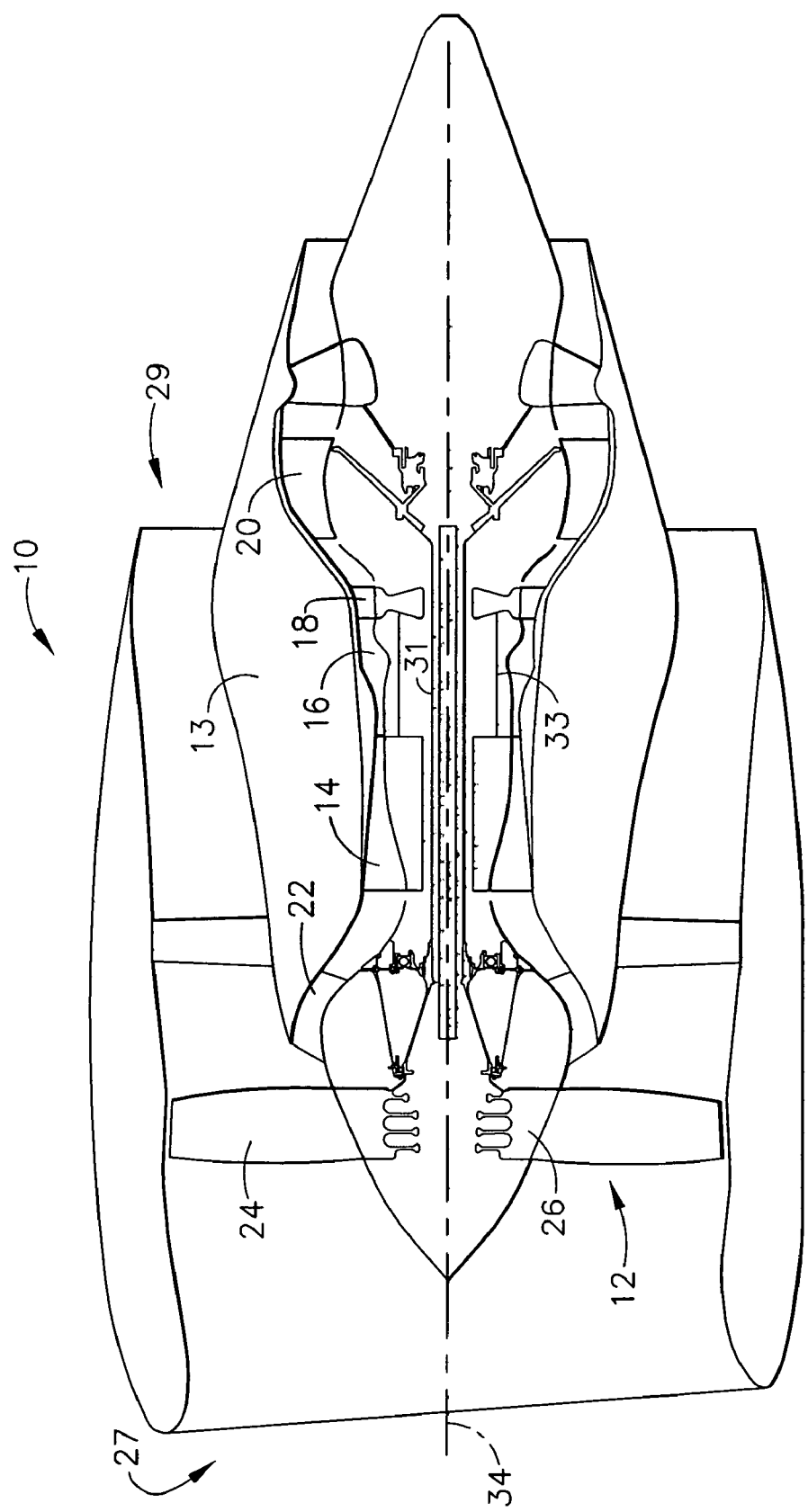
FIG. 5 is a schematic illustration of an exemplary gas turbine engine.

FIG. 5 is a schematic illustration of a gas turbine engine 10 including a fan assembly 12 and a core engine 13 including a high pressure compressor 14, and a combustor 16. Engine 10 also includes a high pressure turbine 18, a low pressure turbine 20, and a booster 22. Fan assembly 12 includes an array of fan blades 24 extending radially outward from a rotor disc 26. Engine 10 has an intake side 27 and an exhaust side 29. In one embodiment, the gas turbine engine is a CF6-50 available from General Electric Company, Cincinnati, Ohio. Fan assembly 12 and turbine 20 are coupled by a first rotor shaft 31, and compressor 14 and turbine 18 are coupled by a second rotor shaft 33.

During operation, air flows axially through fan assembly 12, in a direction that is substantially parallel to a central axis 34 extending through engine 10, and compressed air is supplied to high pressure compressor 14. The highly compressed air is delivered to combustor 16. Airflow (not shown in FIG. 1) from combustor 16 drives turbines 18 and 20, and turbine 20 drives fan assembly 12 by way of shaft 31.

Figure 6:
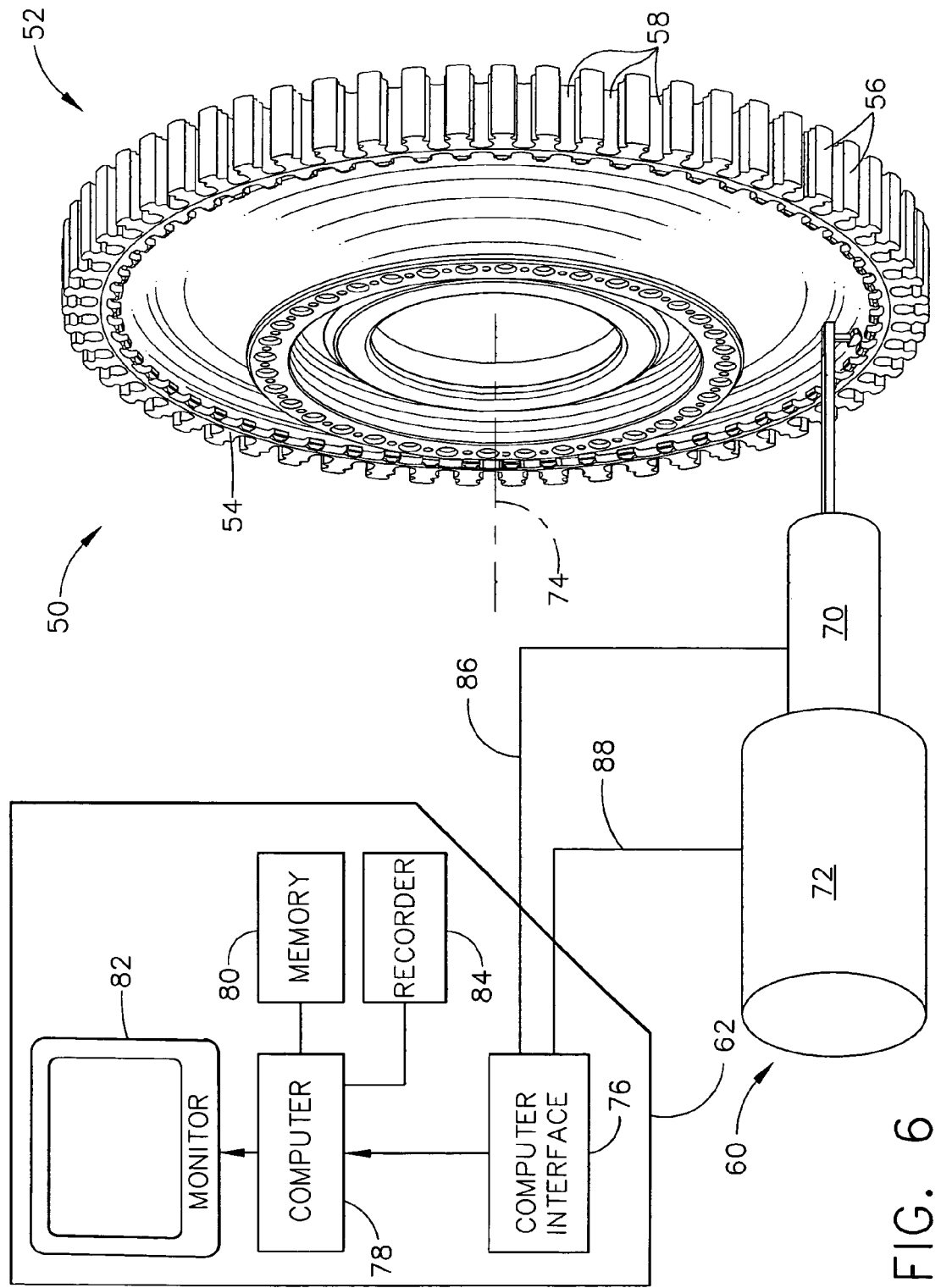
FIG. 6 is a schematic diagram of an exemplary eddy current surface flaw detection system.

FIG. 6 is a schematic diagram of an exemplary eddy current surface flaw detection system 50 that can be used to inspect a component 52 such as, but not limited to, a gas turbine engine disk 54 which may be used with gas turbine engine 10. In the exemplary embodiment, disk 54 includes a plurality of gear teeth 56 and a plurality of dovetail slots 58 defined between gear teeth 56.

Although the methods and apparatus herein are described with respect to gear teeth 56 and dovetail slots 58, it should be appreciated that the methods and apparatus can be applied to a wide variety of components. For example, component 52 may be of any operable shape, size, and configuration. Examples of components may include, but are not limited to, components of gas turbine engines such as seals, flanges, turbine blades, turbine vanes, and/or flanges. The component may be fabricated of any operable base material such as, but not limited to, nickel-base alloys, cobalt-base alloys, titanium-base alloys, iron-base alloys, and/or aluminum-base alloys. More specifically, although the methods and apparatus herein are described with respect to aircraft engine parts, it should be appreciated that the methods and apparatus can be applied to a wide variety of components used within a steam turbine, a nuclear power plant, an automotive engine, or to inspect any mechanical components.

In the exemplary embodiment, detection system 50 includes a probe assembly 60 and a data acquisition/control system 62. Probe assembly 60 includes an eddy current coil/probe 70 and a probe manipulator 72. Eddy current probe 70 and probe manipulator 72 are each electrically coupled to data acquisition/control system 62 such that control/data information can be transmitted to/from eddy current probe 70/probe manipulator 72 and data acquisition/control system 62. In an alternative embodiment, system 50 also includes a turntable (not shown) configured to rotate component 52 around a central axis 74 during the inspection procedure.

Data acquisition/control system 62 includes a computer interface 76, a computer 78, such as a personal computer with a memory 80, and a monitor 82. Computer 78 executes instructions stored in firmware (not shown). Computer 78 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein.

Memory 80 is intended to represent one or more volatile and/or nonvolatile storage facilities that shall be familiar to those skilled in the art. Examples of such storage facilities often used with computer 78 include, but are not limited to, solid state memory (e.g., random access memory (RAM), read-only memory (ROM), and flash memory), magnetic storage devices (e.g., floppy disks and hard disks), and/or optical storage devices (e.g., CD-ROM, CD-RW, and DVD). Memory 80 may be internal to or external to computer 78. Data acquisition/control system 62 also includes a recording device 84 such as, but not limited to, a strip chart recorder, a C-scan, and an electronic recorder that is electrically coupled to either computer 78 and/or eddy current probe 70.

In use, component 52, such as disk 54, is mounted on a fixture (not shown) to secure disk 54 in place during inspection. Eddy current probe 70 is coupled to probe manipulator 72 to position probe 70 within dovetail slots 58 to facilitate enabling substantially all of the interior of dovetail slots 58 to be scanned during inspection. In the exemplary embodiment, probe manipulator 72 is a six-axis manipulator. Eddy current probe 70 is electrically coupled to data acquisition/control system 62 by a data link 86. Eddy current probe 70 generates electrical signals in response to the eddy currents induced within the surface of dovetail slots 58 during scanning of dovetail slots 58 by probe 70. Electrical signals generated by probe 70 are received by data acquisition/control system 62 over a data communications link 86 and are either stored in memory 80 or recorder 84. Computer 78 is also interconnected to probe manipulator 72 by a communications link 88 to facilitate controlling the scanning of dovetail slots 54. A keyboard (not shown) is electrically coupled to computer 78 to facilitate operator control of the inspection of disk 54. In the exemplary embodiment, a printer 40 may be provided to generate hard copies of the images generated by computer 78.

Figure 7:
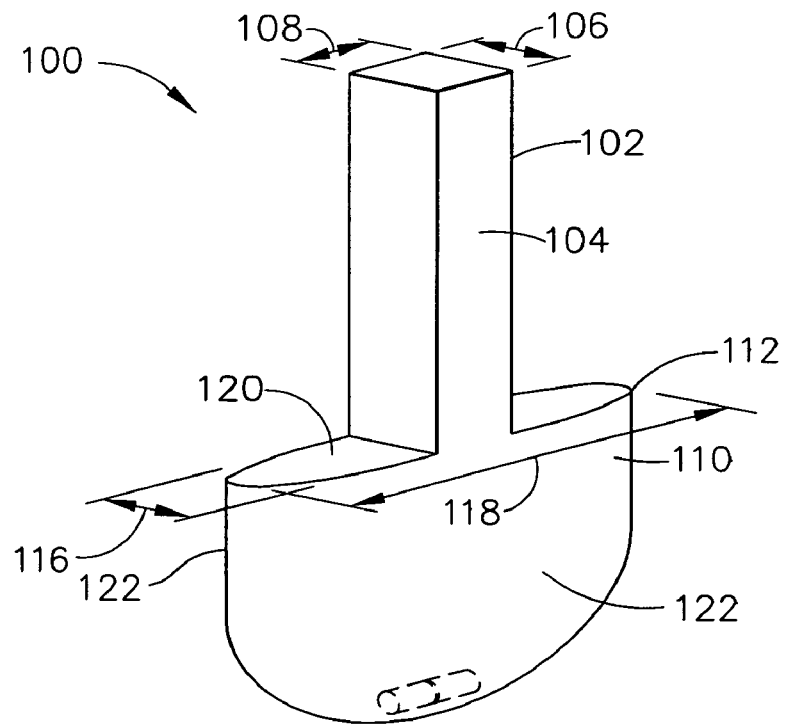
FIG. 7 is a perspective view of an exemplary eddy current probe.
Figure 8:
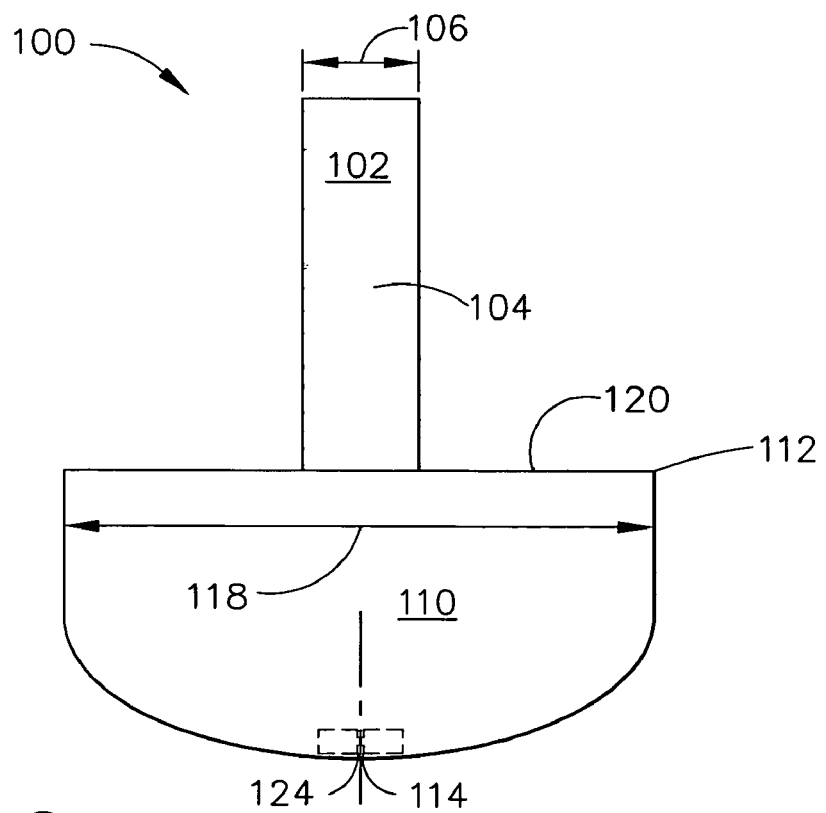
FIG. 8 is a front view of the exemplary eddy current probe shown in FIG. 7.
Figure 9:
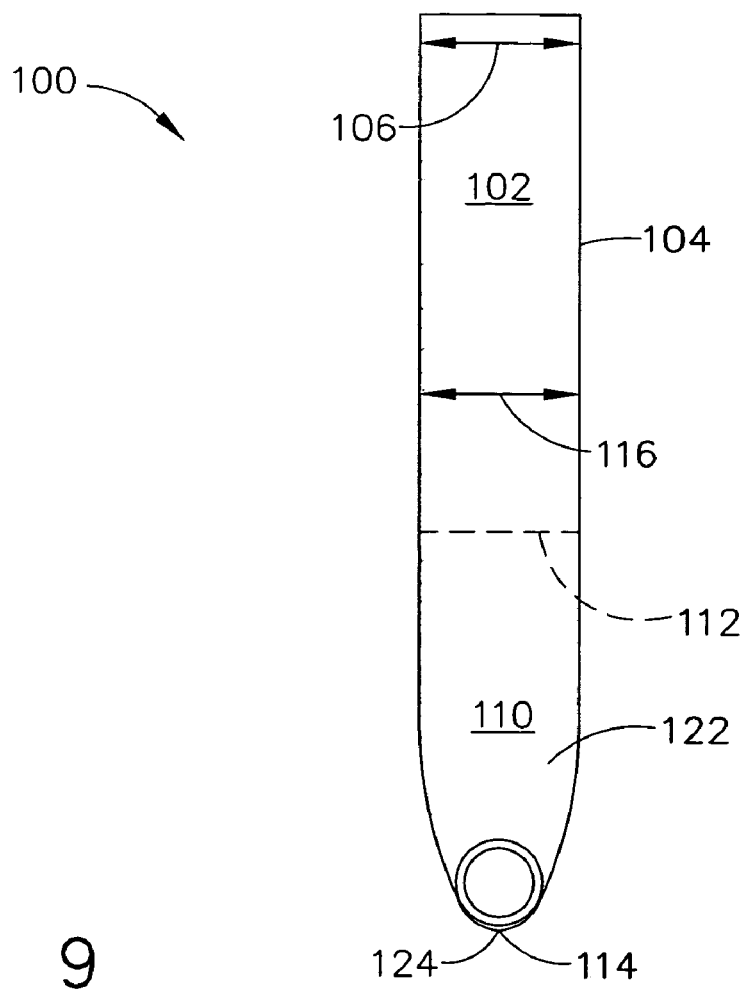
FIG. 9 is a side view of the exemplary eddy current probe shown in FIG. 7.
Figure 10:
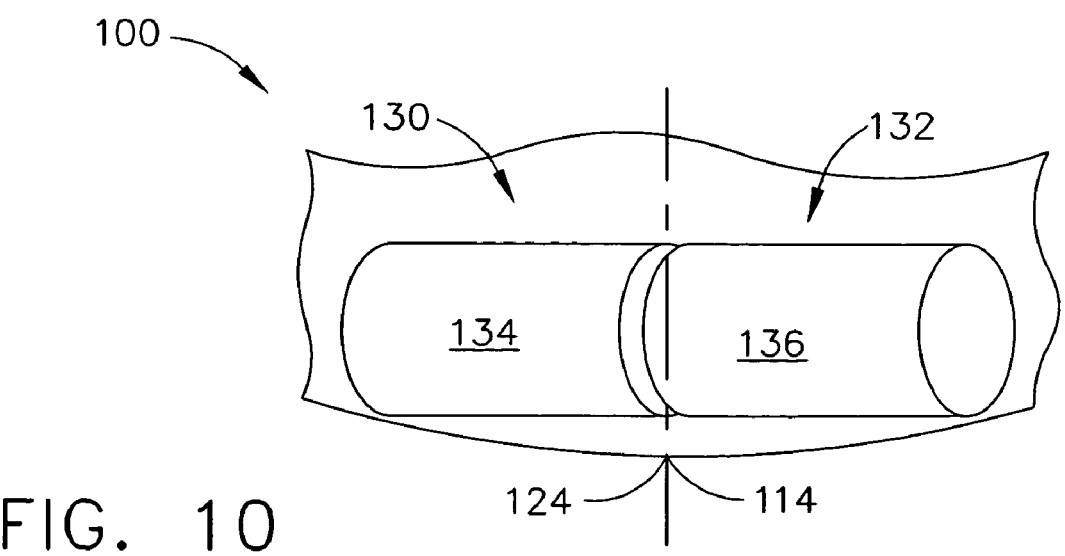
FIG. 10 is a perspective view of the side-mount coils in the exemplary eddy current probe shown in FIG. 7.

FIG. 7 is a perspective view of an exemplary eddy current probe 100 that may be used with eddy current surface flaw detection system 50 (shown in FIG. 6). FIG. 8 is a front view of eddy current probe 100. FIG. 9 is a side view of eddy current probe 100. FIG. 10 is a perspective view of a portion of eddy current probe 100.

Eddy current probe 100 includes a body portion 102 that includes an outer surface 104, a width 106, and a length 108 that is different than width 106. In the exemplary embodiment, body portion 102 is substantially rectangular shaped. Eddy current probe 100 also includes a tip portion 110 that is coupled to body portion 102. In the exemplary embodiment, body portion 102 and tip portion 110 are integrally formed together such that body portion 102 and tip portion 110 form a unitary eddy current probe 100.

Tip portion 110 includes a tip body portion end 112 and a outer tip 114. Tip portion 110 has a width 116 and a length 118 that is greater than length 116. In the exemplary embodiment, width 116 gradually decreases from tip body portion end 112 to outer tip 114, and length 118 gradually decreases from tip body portion end 112 to outer tip 114.

Tip portion 110 also includes an upper surface 120 that is coupled to body 102. In the exemplary embodiment, tip upper surface 120 includes a substantially rectangular surface defined such that tip portion width 116 is substantially similar to body portion width 106, and tip portion length 118 is substantially greater than body length 108. In the exemplary embodiment, tip width 116 and tip length 118 each gradually diminish from tip upper surface 120 such that an apex 124 is formed at outer tip 114.

Eddy current probe 100 also includes a first a probe coil 130 and a second probe coil 132 mounted within tip portion 110. Probe coils 130 and 132 each include a respective substantially cylindrical outer surface 134 and 136 such that at least a portion of probe coils 130 and 132 are positioned adjacent to tip portion lower surface 114. In the exemplary embodiment probe coils 130 and 132 are side-mount coils that are electrically coupled in series. When activated, coils 130 and 132 each generate a magnetic field that is substantially perpendicular to a surface of the component being scanned such as, but not limited to gear teeth 56 and dovetail slots 58. More specifically, probe coils 130 and 132 each transmit a transient electromagnetic flux into component being tested.

In the exemplary embodiment, coils 130 and 132 positioned co-axially, rather than side-by-side. Eddy current probe 100 has a length 118 that is longer than a gap defined between inspection areas in the scan direction, and a width 116 that is shorter in the indexing direction. Coils 130 and 132 are positioned approximately in the center of tip portion 110. Accordingly, eddy current probe 100 includes an approximately spade-shaped tip portion 110 that enables gaps between inspection areas to be traversed without by tip portion 110 falling into the gaps. Moreover, and in the exemplary embodiment, the relatively round bottom of outer tip 114 facilitates coils 130 and 132 being fabricated with a radius of approximately 25 mils. The relatively small size of eddy current probe 100 facilitates probe 100 maintaining a substantially normal contact with relatively sharply contoured surfaces.

Moreover, the unique shape of eddy current probe 100 also facilitates enabling eddy current probe 100 to be oriented at an angle that is approximately 45 degrees to a surface of the component being tested without compromising the EC signal. In contrast, known differential probes are generally only tiltable up to approximately 2 degrees before the EC signal deteriorates. The favorable tilt tolerance of side-mount probe 100 facilitates exemplary components with sharp indexing requirements to be inspected without complex motion control.

Figure 11:
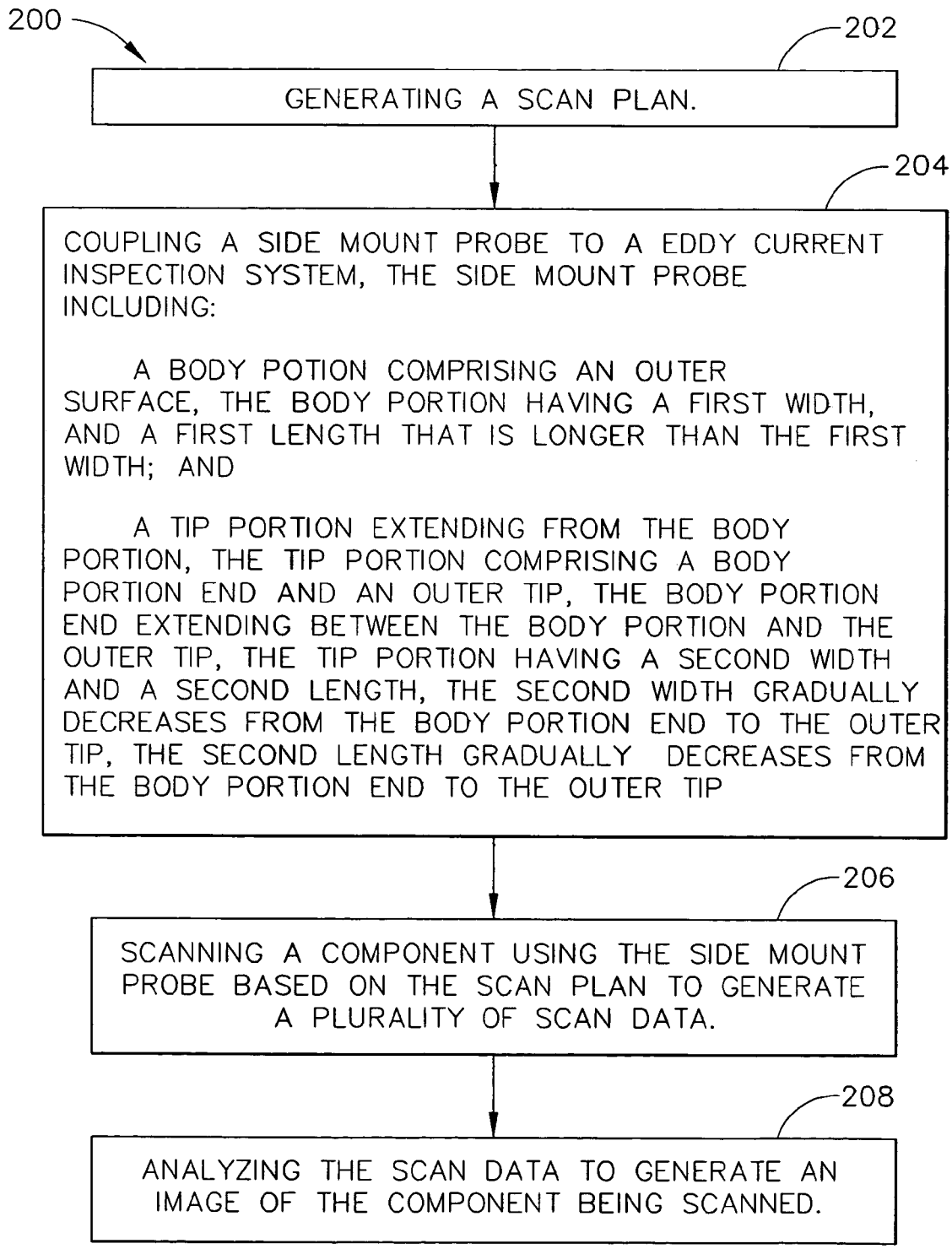
FIG. 11 is a flowchart illustrating an exemplary method for performing an eddy current inspection.

FIG. 11 is a flow chart illustrating an exemplary method 200 of operating eddy current surface flaw detection system 50 and eddy current probe 100. Method 200 includes generating 202 a scan plan of a component to be imaged, coupling 204 a side-mount probe, such as probe 100, to an eddy current inspection system, such as inspection system 50, and analyzing 208 the scan data to generate at least one image of the component being scanned.

Figure 12:
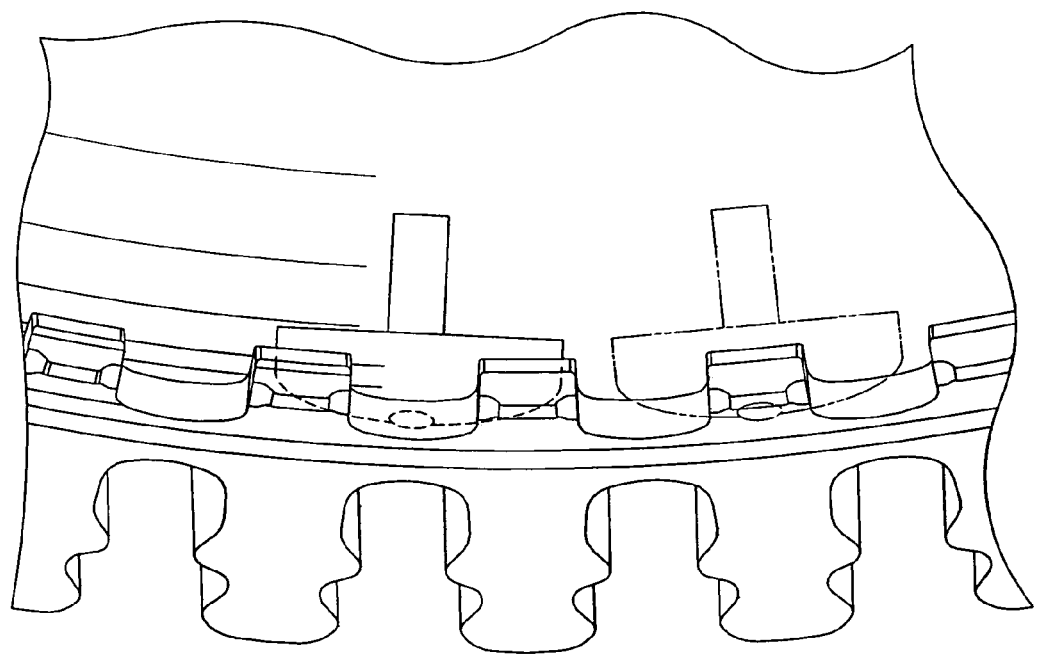
FIG. 12 is a side view of an eddy current probe operating in a scan direction.
Figure 13:
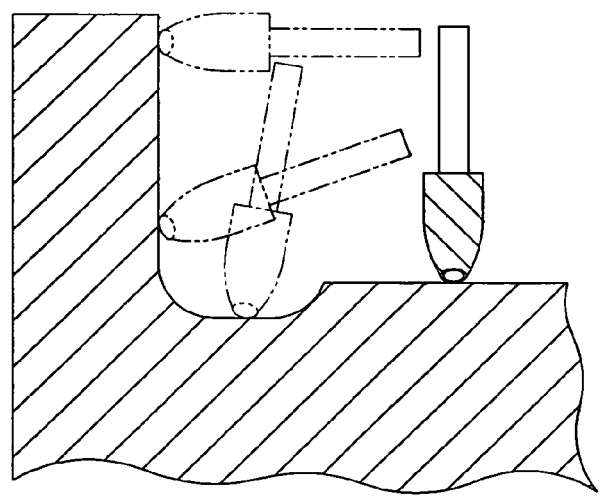
FIG. 13 is a side view of an eddy current probe operating in an indexing direction.
Figure 14A:
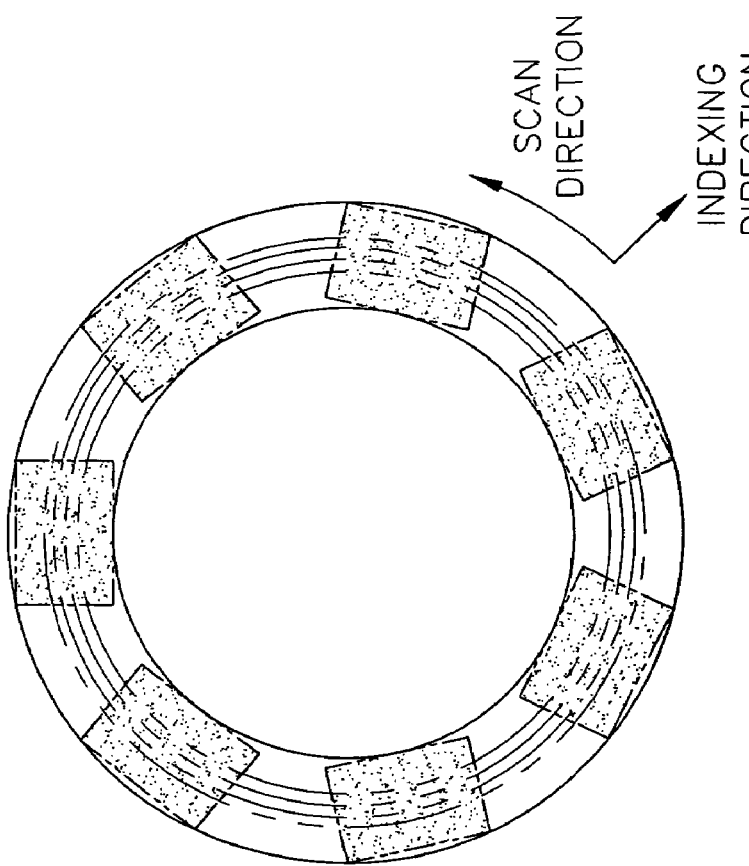
FIGS. 14a and 14b illustrate a scanplan utilizing a side-mount eddy current probe.
Figure 14B:

Generating 202 a scan plan includes generating a scan plan to facilitate directing eddy current probe 100 to scan an inspection area. Scanplan as used herein is defined as a collection of Computer Numeric Control (CNC) commands that direct probe 100 to move along a predetermined line in the scan direction (shown in FIG. 12) while acquiring a signal from eddy current probe 100. At the completion of each scan line, eddy current probe 100 is indexed to the next scan line (shown in FIG. 13) and eddy current probe 100 again is moved along a predetermined line in the scan direction. This process is continued until the scan plan is completed. FIGS. 14a and 14b illustrate a scanplan using side-mount probe 100 wherein a scan line of 360 degree circumferential rotation is illustrated.

In the exemplary embodiment, eddy current probe 100 facilitates contacting the surface of the component being inspected without unwanted lift-off, whereas at least one known eddy current probe has difficulty scanning a component that includes a highly contoured outer surface. Designing a scan plan that is implemented using a known eddy current probe is relatively time consuming since the designer must incorporate expected occurrences of probe lift-off into the scan plan prior to scanning the component. Therefore generating a scanplan that utilizes a known eddy current probe is a relatively time consuming and tedious process to achieve inspection coverage and sensitivity requirements for the tested component.

However, generating a scan plan utilizing eddy current probe 100 facilitates reducing the time and complexity required to develop the scan plan since eddy current probe 100 is capable of tilting or leaning approximately ±/−45 degrees with respect to an absolute normal of the component surface without compromising the eddy current signal. Moreover, generating a scan plan that utilizes eddy current probe 100 facilitates producing a much more robust inspection process that is relatively insensitive to probe to probe or machine to machine variances compared to known inspection processes utilizing a known eddy current probe.

In operation, coupling 204 a side-mount probe, such as probe 100, to an eddy current inspection system includes coupling eddy current probe 100 to probe holder such as probe manipulator 72 (shown in FIG. 6). A rotation axis is then set to zero degrees before the scan starts. The component is then scanned 206 using eddy current probe 100 based on the scan plan to generate a plurality of scan data. Specifically, eddy current inspection system 50 is activated such that the component is scanned in the scanning direction by turning the rotary axis while the probe stays at a fixed position. Eddy current probe 100 then rides over any interrupted gaps on the component until the scan is completed in the scanning direction. At the next zero degree point of rotation, eddy current probe 100 is moved or indexed to the next scan line in the indexing direction. In the exemplary embodiment, the first scan line begins at zero degrees, and each subsequent scan line is registered to this point. The scan of the component proceeds until the scan plan is completed.

Analyzing 208 the scan data to generate at least one image of the component being scanned includes collecting the signals, i.e. scan data, transmitted from eddy current probe 100 after the scan plan is completed, and combining the scan data into at least one two-dimensional (2D) image for analysis. In the exemplary embodiment, the 2D image includes a combination of the signals transmitted from eddy current probe 100 from both the inspection zones and those produced by the interrupted gaps between them. In addition, the 2D image also includes a plurality of edge signals generated from both sides of the inspection zone. For example, when eddy current probe 100 passes an edge of the component, i.e. from air to material, or vice versa, eddy current probe 100 generates a signal that is typically greater than a signal that is generated by the component material, and is therefore generally interpreted by eddy current probe 100 as a material abnormality. To facilitate reducing or minimizing the imaging effects of these signals, the 2D image is divided into a plurality of sub-images that have approximately the same shape. The sub-images are then sent through a registration and subtraction process to minimize the unwanted signals from gaps and edges.

In the exemplary embodiment, filters based on the characteristic crack signatures of the tested component are then applied to the resulting images to facilitate optimizing the segmentation of significant indications from any remaining noise. For example, FIG. 15 illustrates a component image generated using eddy current probe 100 that includes a calibration notch. The image pattern produced by the notch is unique in its gray scale distribution. As eddy current probe 100 passes over the notch, a black-white-black pattern is formed, whereas at least one known eddy current probe generates a checkerboard pattern for the same component. The image pattern of the calibration notch then is utilized to select a matched filter for pattern recognition and detection of significant indications on the component. In the exemplary embodiment, the matched filter is applied to the 2D image data, to facilitate detecting very small indications, down to approximately 10 mil in length.

FIGS. 16a and 16b illustrate an image that is generated of a plate that includes simulated indications before and after image processing. The simulated indications are positioned in the middle of the scan zone and on edges to facilitate validating a detectability of edge cracks. By using the image processing techniques described herein, the edge signals are clearly seen.

The eddy current inspection system described herein generates a scanplan, i.e. the motion control and data acquisition program for the inspection system, scans the component according to the scanplan utilizing a side-mount eddy current probe, and analyzes the scan data. Accordingly, the method and apparatus described herein facilitate enabling interrupted features of a component to be inspected in a continuous fashion, thereby minimizing the amount of time needed to acquire and process the data compared to known eddy current inspection systems, without having any adverse affects on the sensitivity of the inspection. Moreover, the eddy current inspection system and probe described herein facilitate inspecting a component that includes interrupted features because eddy current inspection system 50 includes side-mount probe 100 that is relatively immune to the surface normal requirement.

The above-described methods and apparatus provide a cost-effective and reliable means to facilitate reducing the amount time needed to perform an eddy current inspection on a component under test. Specifically, the method and apparatus described herein facilitates reducing an inspection time and improve an eddy current system performance by utilizing a continuous scan data acquisition method that eliminates the time consuming raster scans typically used in single coils applications. The eddy probe described herein includes a side-mount differential coil that is less sensitive to orientation than known eddy current probes, and can be therefore maintain consistent image quality, ensuring sensitivity.

Exemplary embodiments of digital eddy current inspection systems are described above in detail. The systems are not limited to the specific embodiments described herein, but rather, components of each system may be utilized independently and separately from other components described herein. Each system component can also be used in combination with other system components. More specifically, although the methods and apparatus herein are described with respect to aircraft engine parts, it should be appreciated that the methods and apparatus can also be applied to a wide variety of components used within a steam turbine, a nuclear power plant, an automotive engine, or to inspect any mechanical component.

While the invention has been described in terms of various specific embodiments, those skilled in the art will recognize that the invention can be practiced with modification within the spirit and scope of the claims.

What is claimed is:

1. A method for inspecting a component, said method comprising:
   generating a scan plan of a component to be inspected;
   coupling a side-mount probe to an eddy current inspection system;
   inducing an eddy current into the component;
   measuring the eddy current in the component to generate a plurality of scan data; and
   analyzing the scan data to generate at least one image of the component being inspected.

2. A method in accordance with claim 1 wherein coupling a side-mount probe to an eddy current inspection system further comprises coupling a side-mount probe to the eddy current inspection system, the probe includes a body portion comprising an outer surface, said body portion having a width and a length that is longer than the width, and a tip portion extending from the body portion, the tip portion comprising an end and an outer tip, the end extending between the body portion and the outer tip, the tip portion having a width and a length wherein the width gradually decreases from the end to the outer tip, the second length gradually decreases from the end to the outer tip.

3. A method in accordance with claim 2 further comprising coupling a side-mount probe to the eddy current inspection system, the side-mount probe includes at least two coils mounted within the tip portion, each of the at least two coils comprising a substantially cylindrical shape, at least a portion of each of the coils is positioned adjacent to the tip portion outer tip for generating a magnetic field that is substantially perpendicular to a surface of the component being inspected.

4. A method in accordance with claim 1 wherein measuring the eddy current further comprises positioning the eddy current probe at an angle that is greater than approximately 5 degrees to a normal surface of the component being inspected.

5. A method in accordance with claim 1 wherein generating a scan plan further comprises generating a plurality of computer numeric control commands.

6. A method in accordance with claim 1 wherein analyzing the scan data further comprises utilizing the scan data to generate at least one two-dimensional image of the component being inspected.

7. A method in accordance with claim 6 further comprising dividing the two-dimensional image into a plurality of sub-images that each have approximately the same shape.

8. A method in accordance with claim 7 further comprising processing at least one sub-image to facilitate reducing signals acquired from at least one of a component edge and a component gap using a registration and subtraction process to generate a third image.

9. A method in accordance with claim 8 further comprising selecting a filter based on the third image generated and filtering the third image to generate a final image.

10. A side-mount eddy current probe for inspecting a component, said eddy current probe comprising:
    a body portion comprising an outer surface and having a width, and a length that is longer than said width; and
    a tip portion extending from said body portion, said tip portion comprising an end and an outer tip, said end extending between said body portion and said outer tip, said tip portion having a width and a length, said tip portion width gradually decreases from said tip portion end to said outer tip, said tip portion length gradually decreases from said tip portion end to said outer tip.

11. An eddy current probe in accordance with claim 10 further comprising at least two coils mounted within said tip portion, each of said at least two coils comprises a substantially cylindrical shape, at least a portion of each of said at least two coils is positioned adjacent to said tip portion outer tip for generating a magnetic field that is substantially perpendicular to a surface of the component being inspected.

12. An eddy current probe in accordance with claim 10 further comprising at least two side-mount coils mounted within said tip portion, each of said at least two side-mount coils comprises a substantially cylindrical shape, at least a portion of each said side-mount coil is positioned adjacent to said tip portion outer tip for generating a magnetic field that is substantially perpendicular to a surface of the component being scanned.

13. An eddy current probe in accordance with claim 10 wherein said body portion and said tip portion are formed unitarily together.

14. An eddy current inspection system comprising:
an eddy current probe comprising:
a body portion comprising an outer surface and having a width, and a length that is longer than said width; and
a tip portion extending from said body portion, said tip portion comprising an end and an outer tip, said end extending between said body portion and said outer tip, said tip portion having a width and a length, said tip portion width gradually decreases from said end to said outer tip, said tip portion length gradually decreases from said end to said outer tip; and
a data acquisition/control system coupled to said eddy current probe and configured to record an output received from said eddy current probe.

15. A system in accordance with claim 14 wherein said component is a gas turbine engine component.

16. A system in accordance with claim 14 wherein said eddy current probe further comprises at least two coils mounted within said tip portion, each of said at least two coils that each comprise a substantially cylindrical shape, at least a portion of said at least two coils is positioned adjacent to said tip portion outer tip for generating a magnetic field that is substantially perpendicular to a surface of the component being inspected.

17. A system in accordance with claim 14 wherein said data acquisition/control system is further configured to generate a plurality of computer numeric control commands.

18. A system in accordance with claim 14 wherein said data acquisition/control system is further configured to utilize the scan data to generate at least one two-dimensional image of the component.

19. A system in accordance with claim 18 wherein said data acquisition/control system is further configured to divide the at least one two-dimensional image into a plurality of sub-images that each have approximately the same shape, and process at least one sub-image to facilitate reducing signals acquired from at least one of a component edge and a component gap using a registration and subtraction process to generate a third image.

20. A system in accordance with claim 19 wherein said data acquisition/control system is further configured to select a filter based on the third image generated and filtering the third image to generate a final image.

* * * * *